(12) United States Patent
Friesz

(10) Patent No.: US 9,221,777 B2
(45) Date of Patent: Dec. 29, 2015

(54) PROCESS FOR PREPARATION OF DRONEDARONE BY THE USE OF DIBUTYLAMINOPROPANOL REAGENT

(71) Applicant: Sanofi, Paris (FR)

(72) Inventor: Antal Friesz, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/372,661

(22) PCT Filed: Mar. 1, 2013

(86) PCT No.: PCT/IB2013/000915
§ 371 (c)(1),
(2) Date: Jul. 16, 2014

(87) PCT Pub. No.: WO2013/128294
PCT Pub. Date: Sep. 6, 2013

(65) Prior Publication Data
US 2015/0018568 A1    Jan. 15, 2015

(30) Foreign Application Priority Data

Jan. 20, 2012  (EP) .................................. 12462002

(51) Int. Cl.
*C07D 307/80*    (2006.01)
(52) U.S. Cl.
CPC ..................................... *C07D 307/80* (2013.01)
(58) Field of Classification Search
CPC ...................................................... C07D 307/80
USPC ................................................. 549/456, 468
See application file for complete search history.

(56) References Cited

U.S. PATENT DOCUMENTS

| | | | |
|---|---|---|---|
| 3,577,441 A | 5/1971 | Kaminsky et al. | |
| 3,657,350 A | 4/1972 | Mooradian et al. | |
| 3,937,737 A | 2/1976 | Eiglmeier | |
| 4,243,405 A | 1/1981 | Balasubramanyan et al. | |
| 4,666,931 A | 5/1987 | Ohishi et al. | |
| 5,066,803 A | 11/1991 | D'Ambra et al. | |
| 5,223,510 A | 6/1993 | Gubin et al. | |
| 6,555,697 B1 | 4/2003 | Schlama | |
| 6,828,448 B2 | 12/2004 | Fino et al. | |
| 6,846,936 B2 | 1/2005 | Biard | |
| 6,855,842 B1 | 2/2005 | Schlama et al. | |
| 6,949,583 B2 | 9/2005 | Assens et al. | |
| 6,984,741 B2 | 1/2006 | Magerlein | |
| 7,148,240 B2 | 12/2006 | Assens et al. | |
| 7,312,345 B2 | 12/2007 | Gutman et al. | |
| 7,517,876 B2 | 4/2009 | Klein et al. | |
| 8,143,269 B2 | 3/2012 | Whitten et al. | |
| 8,501,971 B2* | 8/2013 | Friesz et al. | 549/488 |
| 8,658,808 B2 | 2/2014 | Kretzschmar et al. | |
| 8,658,809 B2* | 2/2014 | Friesz et al. | 549/468 |
| 8,674,121 B2 | 3/2014 | Kretzschmar et al. | |
| 8,686,180 B2 | 4/2014 | Bon et al. | |
| 8,748,636 B2 | 6/2014 | Bailly et al. | |
| 8,796,489 B2 | 8/2014 | Bailly et al. | |
| 8,816,103 B2* | 8/2014 | Friesz et al. | 549/468 |
| 8,871,956 B2 | 10/2014 | Bailly et al. | |
| 8,884,033 B2 | 11/2014 | Bon et al. | |
| 8,889,734 B2 | 11/2014 | Friesz et al. | |
| 8,962,869 B2* | 2/2015 | Grimaud et al. | 549/468 |

(Continued)

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

Zasshi, Y. (1956). "Studies on the Syntheses of Phenothlazine Derivatives, I. Syntheses of N-Substituted Phenothiazines by Tosylates," *J. Pharm. Soc. of Japan* 76:637-640 (with English Translation).

(Continued)

*Primary Examiner* — Golam M M Shameem
(74) *Attorney, Agent, or Firm* — Morrison & Foerster LLP

(57) ABSTRACT

The invention relates to a novel process for preparation of dronedarone of formula (I) and pharmaceutically acceptable salts thereof, characterized in that a compound of formula (II)—where L is leaving group—is reacted with compound of formula (III) and the obtained product is isolated and, if desired, converted into a pharmaceutically acceptable salt thereof.

(I)

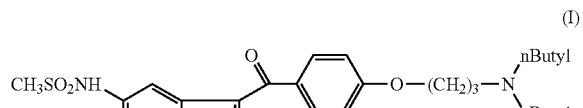

(II)

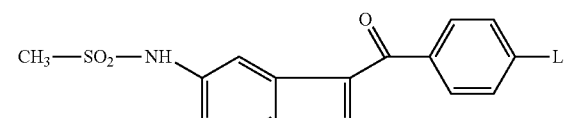

(III)

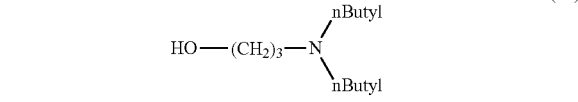

5 Claims, No Drawings

(56) References Cited

U.S. PATENT DOCUMENTS

| | | | |
|---|---|---|---|
| 2008/0033209 A1 | 2/2008 | Szarvas et al. |
| 2010/0087415 A1 | 4/2010 | Whitten et al. |
| 2010/0273764 A1 | 10/2010 | Andrews et al. |
| 2013/0023678 A1 | 1/2013 | Priem et al. |
| 2013/0109868 A1 | 5/2013 | Friesz |
| 2014/0018553 A1 | 1/2014 | Grimaud et al. |
| 2014/0018554 A1 | 1/2014 | Friesz et al. |
| 2014/0081035 A1 | 3/2014 | Friesz et al. |
| 2014/0114081 A1 | 4/2014 | Friesz et al. |
| 2015/0005515 A1 | 1/2015 | Friesz et al. |
| 2015/0031901 A1 | 1/2015 | Bon et al. |
| 2015/0031902 A1 | 1/2015 | Huszar et al. |

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO-02/48078 A1 | 6/2002 |
| WO | WO-02/48132 A1 | 6/2002 |
| WO | WO-03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Ando, M.E. et al. (1982). "Motion at the Active Site of Tosylchymotrypsin," *Journal of the American Chemical Society* 104(11):3172-3178.

International Search Report mailed on Sep. 16, 2013, for PCT Patent Application No. PCT/IB2013/000915, filed on Mar. 1, 2013, five pages.

March, J. (Jul. 1, 1992), "Aromatic Electrophilic Substitution," Chapter 11 in *Advanced Organic Chemistry, Reactions, Mechanism and Structure*, 4$^{th}$ edition, Wiley Interscience, pp. 538-542.

Munch, R. et al. (1946). "The Preparation of Some α-Dialkylamino-ω-Methylaminoalkanes," *J. Am. Chem. Soc.* 68:1297-1299.

Ślusarska, E. et al. (Feb. 1981). "One-Pot Phase-Transfer-Catalysed N-Alkylation of Diphenylphosphinamide with Alcohols in the Presence of Methanesulfonyl Chloride," *Synthesis* 155-156.

Written Opinion of the International Searching Authority mailed on Sep. 16, 2013, for PCT Patent Application No. PCT/IB2013/000915, filed on Mar. 1, 2013, five pages.

Abramenko, et al., Polymethine Dyes—Furo[2,3-g] Benzothiazole Derivatives, Chemistry of Heterocyclic Compounds, vol. 11, (1975), pp. 1361-1364.

Adams, R. et al. Quinone imides. IV. P-Quinone monosulfonimides. Journal of the American Chemical Society. 1951, vol. 73, pp. 1145-1149.

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz, Lilian et al., "Novel N-Aryl and N-Heteroaryl Sulfamide Synthesis via Palladium Cross Coupling," Organic Letters (2004), vol. 6, No. 16, pp. 2705-2708.

Anjanappa, Prakash et al., "2-(Trimethylsilyl)ethanesulfonyl amide as a new ammonia equivalent for palladium-catalyzed amination of aryl halides," Tetrahedron Letters (2008), vol. 49, pp. 4585-4587.

Bartoli, G. et al. (1991). "Unexpected Elimination to α,β-Alkynylketones in the Reaction of Dianions of 1-Arylenaminones with Trimethylchlorosilane," Tetrahedron Letters 32(48):7091-7092.

Batra, S. et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli, Shanthaveerappa K. et al., "Application of Ionic Liquid Halide Nucleophilicity for the Cleavage of Ethers: A Green Protocol for the Regeneration of Phenols from Ethers," Journal of Organic Chemistry (2004), vol. 69, pp. 3340-3344.

Bourgery, et al., Synthesis and Antiarrhythmic Activity of New Benzofuran Derivatives, Journal of Medicinal Chemistry, (1981), vol. 24, No. 2, pp. 159-167.

Burton, George et al., "Palladium-Catalyzed Intermolecular Coupling of Aryl Chlorides and Sulfonamides under Microwave Irradiation," Organic Letters (2003), vol. 5, No. 23, pp. 4373-4376.

Castellino, Angelo J. et al., "Synthesis of Benzofurans from Oxygenated Phenoxyamines," Journal of Organic Chemistry (1984), vol. 49, pp. 4399-4404.

Chauhan, Shive M.S. et al., "Microwave assisted dealkylation of alkyl aryl ethers in ionic liquids," Journal of Chemical Research (2004), p. 693-694.

Cheng, Lili et al., "Facile Cleavage of Ethers in Ionic Liquid," Bulletin of the Chemical Society of Japan (2007), vol. 80, No. 10, pp. 2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," *Current Topics in Catalysis* 6:19-33.

Denmark, S.E. et al. (2008). "Lewis base catalysis in organic synthesis," *Angew. Chem. Int. Ed.* 47(9):1560-1638.

Douglass, I.B. (1959). "Some New Reactions of Methanesulfenyl Chloride," *Journal of Organic Chemistry* 24:2004-2006.

Fennel, EA. (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

(56) References Cited

OTHER PUBLICATIONS

Gilow, H.M. et al. (Jun.-Jul. 1991). "Sulfenylation of Some Pyrroles and Indoles," *J. Het. Chem.* 28:1025-1034.
Groves, J.K. (1972). "The Friedel—Crafts Acylation of Alkenes," Chem. Soc. Rev. 1:73-97.
Gutowski, Keith E. et al "Prediction of the Formation and Stabilities of Energetic Salts and Ionic Liquids Based on ab Initio Electronic Structure Calculations," The Journal of Physical Chemistry B (2005), vol. 109, pp. 23196-23208.
Haddadin et al. (1976). "Reaction to Benzofurazan Oxide with Unsymmetrical 1, 3-Diketones: Steric Polar Effects," *Tetrahedron* 32:719-724.
Hauser, CR. et al. (1948) "Alkaline cleavage of unsymmetrical β-diketones. Ring opening of acylcyclohexanones to form ε-acylcaproic acids," Journal of the American Chemical Society. 70:4023-4026.
Headley, Lindsay Sanders et al., "Dynamic Solvation in Imidazolium-Based Ionic Liquids on Short Time Scales," Journal of Physical Chemistry (2006), vol. 110, pp. 9549-9554.
Horton et al. (1967). "Reactions With Reactive Alkyl Halides," *J. Meth. In Enzymology* 11:556-565.
Ikawa, Takashi et al., "Pd-Catalyzed Amidations of Aryl Chlorides Using Monodentate Biaryl Phosphine Ligands: A Kinetic, Computational, and Synthetic Investigation," Journal of the American Chemical Society (2007), vol. 129, pp. 13001-13007.
Imori et al. (2006). "Efficient Demethylation of N, N-Dimethylanilines with Phenyl Chloroformate in Ionic Liquids," *Synlett.* 16:2629-2632.
Johnson Matthey Handbook of Pharmaceutical Catalysis, 2009, pp. 1-106.
Joshi, KC. et al. (1986). "Some New Fluorinated β-Ketoamines and Their Copper Complexes," Synth. React. Inorg. Met.-Org. Chem. 1986, vol. 16(7):1009-1024.
Krongauz, ES. et al. Poly(anilophenylquinoxaline)s. Inst. Elementoorg. Soedin. 1986, vol. 28(4), p. 771 (Abstract).
Kurti, L. et al. Strategic Applications of Named Reactions in Organic Synthesis. El Sevior. 2005, pp. 448-449.
Kwiatkowski, E. et al. (1978). Metal Benzoylpivaloylmethanates, Part I. Free Ligands and Copper(II) Chelates. Transition Met. Chem. 3:305-308.
Laszlo, Pierre et al., "Catalysis of Friedel-Crafts Alkylation by a Montmorillonite Doped with Transition-Metal Cations," Helvetica Chimica Acta (1987), vol. 70, pp. 577-586.
Liu, Tao et al., "Cleavage of Methyl Ethers of Flavones by Chloroaluminate Ionic Liquid," Synthetic Communications (2004), vol. 34, pp. 3209-3218.
Majdik (1985). "Studiul reactiei de ciclizare a ortohidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March, J. (Jul. 1, 1992). "Aliphatic Nucleophilic Substitution," Part 2 in *Advanced Organic Chemistry, Reactions, Mechanism and Structure, 4th edition*, Wiley Interscience, pp. 442.
Marvel, C.S. et al. (1941). "Diphenylacetic Acid," *Org. Synth. Coll.* vol. 1, 224-225.
Mehrotra, PK. et al. (2001). Search for new chemical entities as menses inducing agents. Contraception. 64:187-191.
Nagy et al. (2007). "Isomorphous Substitution in Zeolites," *Mol. Sieves* 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.

Pal et al., "Synthesis of monohydroxy-functionalized triphenylene discotics: green chemistry approach," Tetrahedron (2007), vol. 63, pp. 6874-6878.
Roshchin, et al., Synthesis of Benzofurans via Pd2+-Catalyzed Oxidative Cyclization of 2-Allylphenols, Journal of Organometallic Chemistry. vol. 560, No. 1-2. (1998), pp. 163-167.
Sanfilippo, P.J. (1988). "Synthesis of (aryloxy)alkylamines. 1. Novel antisecretory agents with H+K+-ATPase inhibitory activity," *J. Med. Chem.* 31(9):1778-1785.
Serajuddin, ATM. Salt formation to improve drug solubility. Advanced Drug Delivery Reviews 2007, vol. 59, pp. 603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry, vol. 208, pp. 234-237.
Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Son, J-K. et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.
Sun, Lo. et al. N-{2-[2-( 4-Phenylbutyl)benzofuran-4-yl]cyclopropylmethyl}-acetamide: an orally bioavailable melatonin receptor agonist. Bioorganic & Medicinal Chemistry Letters. 2004, vol. 14, pp. 5157-5160.
Tanaka, M. (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber, C. W. (1979). "Isosterism and molecular modification in drug design." Chem. Soc. Rev. 8:563-580.
Upthagrove, A.L. et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser, CC. et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman, Steven A. et al., "Recent advances in ether dealkylation," Tetrahedron (2005), vol. 61, pp. 7833-7863.
Weitkamp et al. (1986). "Isomorphe Substitution in Zeolithen: Katalyse an Boro-, Alumo-und Galio-Silicaten mit ZSM-S-Strukter," *Chem. Ing. Tech.* 58(12):969-971 (with English Translation).
Wikipedia. (Nov. 5, 2012). "Reduction of Nitro Compounds."
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts, G.M., Greene's Protective Groups in Organic Synthesis, Fourth Edition, 2006, John Wiley and Sons, Chapter 7, Protection for the Amino Group, pp. 696-926.
Yang, H. et al. (2009). "Structure-based virtual screening for identification of novel 11 β-HSD1 inhibitors," European J. of Medicinal Chem. 44(3):1167-1171.
Yin, Jingjun et al., "Palladium-Catalyzed Intermolecular Coupling of Aryl Halides and Amides," Organic Letters (2000), vol. 2, No. 8, pp. 1101-1104.
Yin, Jingjun et al., "Pd-Catalyzed Intermolecular Amidation of Aryl Halides: The Discovery that Xantphos Can be Trans-Chelating in a Palladium Complex," Journal of the American Chemical Society (2002), vol. 124, pp. 6043-6048.
U.S. Appl. No. 14/377,484, filed Aug. 7, 2014, by Huszar et al.
U.S. Appl. No. 14/403,528, filed Nov. 24, 2014, by Huszar et al.

* cited by examiner

PROCESS FOR PREPARATION OF DRONEDARONE BY THE USE OF DIBUTYLAMINOPROPANOL REAGENT

CROSS-REFERENCE TO RELATED APPLICATIONS

This application is a National Phase application under 35 U.S.C. §371 of International Application No. PCT/IB2013/000915 filed Mar. 1, 2013 and claims the benefit of EP Application No. 12462002.2 filed Jan. 20, 2012, the disclosures of which are incorporated herein by reference in their entirety.

FIELD OF THE INVENTION

This invention relates to a novel process for the preparation of dronedarone and pharmaceutically acceptable salts thereof, to novel intermediary compounds used in this process and their preparation.

TECHNICAL BACKGROUND

Dronedarone is a known drug for the treatment of arrhythmia and has the chemical name of N-[2-n-butyl-3-[4-[3-(di-n-butylamino)propoxy]benzoyl]benzofuran-5-yl]methane-sulfon-amide [see also formula (I) below]. There are some known processes for the preparation of dronedarone as follows:

In EP 0471609 the following scheme is disclosed for the preparation of dronedarone [Process A]

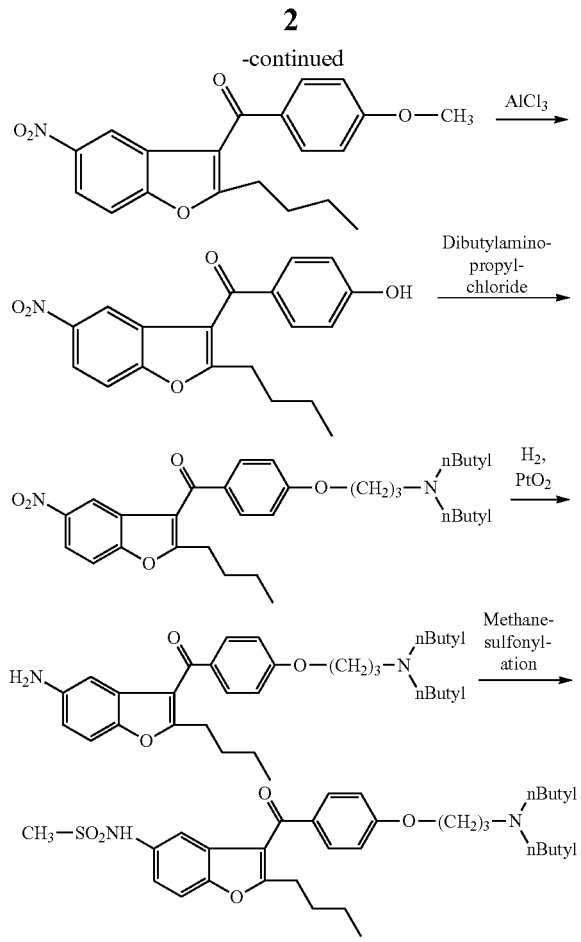

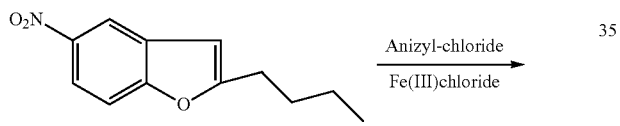

The above mentioned patent description discloses some new intermediary compounds, too.

In WO 02/48078 the following scheme is disclosed for the preparation of dronedarone [Process B]:

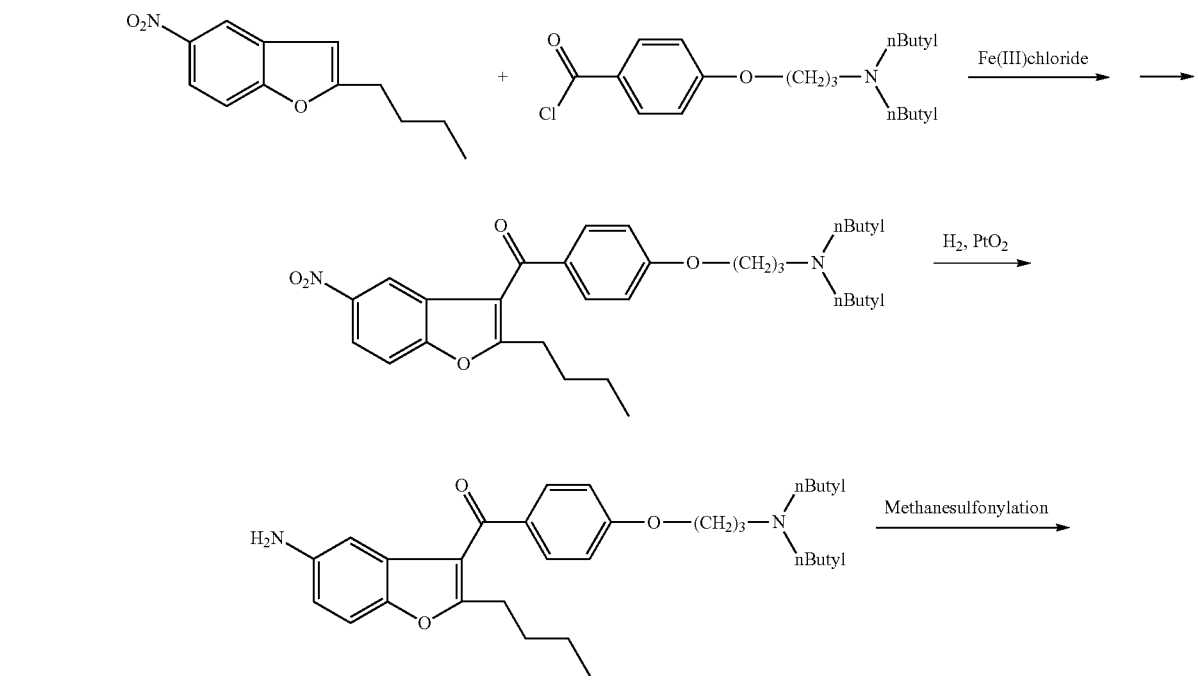

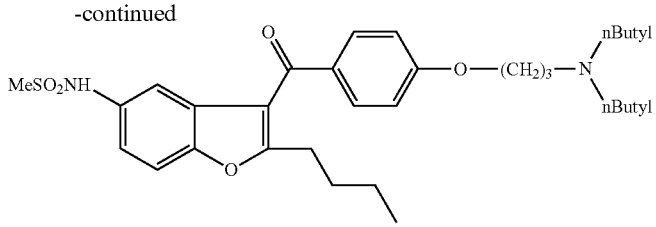

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so called superconvergent route. In the first step of it 5-amino-2-butyl-benzofuran

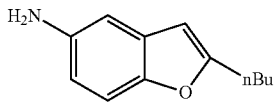

is mesylated and the obtained 2-butyl-5-methanesulfonamido-benzofuran (in HCl salt form) is further reacted in the next step as follows:

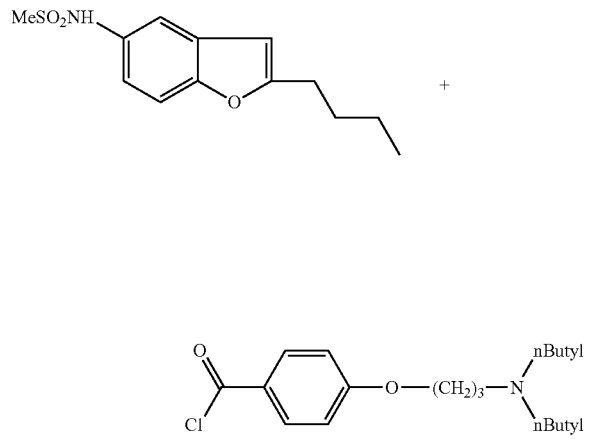

In this process the order of reaction steps are altered, the reduction and the methansulfonylation steps are performed at the beginning of the procedure. Besides the reaction route for preparation of dronedarone, the starting material 2-butyl-5-methansulfonamido-benzofuran and its preparation is also claimed.

From among the mentioned procedures the first one [Process A] is the so called linear synthesis. In this way of procedure the different parts of the dronedarone are stepwise built up on the starting compound. This method is the least economical because the step by step building of the chemical groups is performed where more and more complicated and expensive molecules are applied which rises the costs of preparation. Furthermore, it comprises complicated and dangerous reaction step because aluminium chloride is used in the cleaving reaction of the methoxy group which makes the industrial feasibility more complicated.

In WO 02/48078 (Process B) a shorter synthetic route is disclosed which makes this process more economical, but its last reaction step remained the methansulfonylation reaction of the amino group. This reaction step (see the method described in example 6 of WO 02/48078) is complicated and give a low yield, only 61.6%. Pure product can be obtained after purification using chromatographic column purification, which method is necessary because of the separation difficulties of the bis-methanesulfonylated product.

The process disclosed in WO 02/48132 (process C) is simpler and more economical taken into consideration the number of the reaction steps. Unfortunately, in the last reaction step rather impure dronedarone.HCl (hydrochloride) is formed which is the obvious consequence of the presence of dibutylamino group in the Friedel-Crafts reaction. According to Examples 3 and 4, the crude dronedarone hydrochloride salt is prepared with a yield of 90% which was further purified and finally the crude dronedarone base was produced with a yield of 86%. This base is reacted with hydrogen chloride gas dissolved in isopropanol which results in pure dronedarone hydrochloride salt. No yield was given for this reaction step. According to example 5 crude dronedarone hydrochloride salt was prepared with a yield of 90%, which was washed with water and reacted with hydrogen chloride gas dissolved in isopropanol, resulting dronedarone hydrochloride salt again. The quality of this product is not known. However, neither the components used in the Friedel-Crafts reaction nor the resulted products and by-products are soluble in water, the washing step with water cannot result any purification apart from the removal of inorganic salts.

It is an object of present invention to provide a novel process for the preparation of dronedarone of formula (I). Starting with known and commercially available materials, applying simple and environmentally compatible reagents and solvents to afford high overall yields and good purity of the product.

SUMMARY OF THE INVENTION

The main aspect of the invention is a process for preparation of dronedarone (I) and pharmaceutically acceptable salts thereof

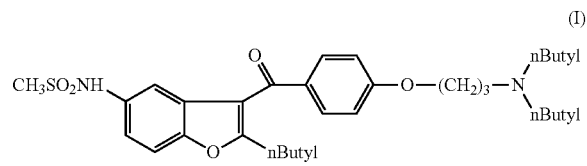

wherein the compound of formula (II)

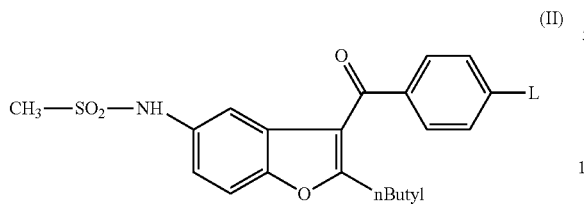

where L is leaving group—is reacted with compound of formula (III)

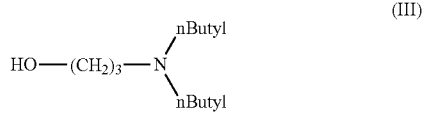

and the obtained product is isolated and, if desired, converted into a pharmaceutically acceptable salt thereof.

This new procedure avoids the drawbacks of the procedures mentioned before, because the intermediates are easily to prepare and the starting materials are not expensive to purchase. In the final step the dibutylamino-ethanol can be removed from the other components easily and the other by-products can be removed very effectively using chromatographic purification or salt forming. In the final reaction used compounds of formula (II) are new and can be prepared using known methods (Yakugaku Zasshi (1956) 76, 637-40; J. Am. Chem. Soc. vol 104. No 11.3173; Synthesis (1981), 155.)

The starting compound of structure (VIII) is known [EP 0471 609, Sanofi]. Some intermediary compounds used in synthesis of dronedarone are new. Dibutylamino-propanol is known in the literature and can be prepared according to the process described in Journal of the American Chemical Society 1946, (7), 1297-99. Further aspects of the invention are the novel intermediary compounds and the methods for the preparation thereof (see below in the "Detailed description of the invention" part). The applied other starting materials are available from commercial sources.

DETAILED DESCRIPTION OF THE INVENTION

Therefore the present invention relates to a process for the preparation of dronedarone and pharmaceutically acceptable salts thereof. The whole process—starting from compounds available commercial sources—reads as follows:

A) For the preparation of compound of formula (VII)

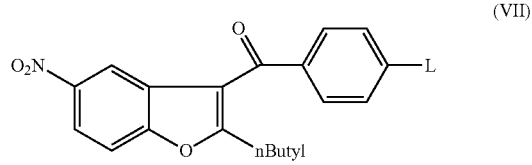

the compound of formula (VIII)

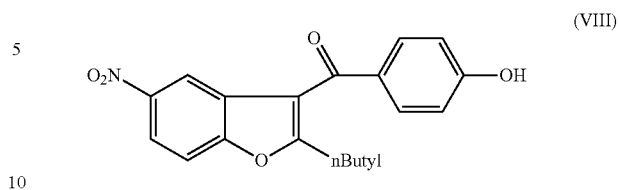

is reacted with activated form of a compound of HO—SO$_2$—L''' (IX), where L''' is leaving group, for example alkyl (e.g. methyl), halogenated alkyl (e.g. trifluoromethyl), aryl (e.g. phenyl), optionally substituted with halogen, alkyl, alkoxy or nitro group.

The "activated form" of compound (IX) is for example a halogenide derivative thereof (OH changed for halogen) or anhydride form of compound (IX).

The reaction is carried typically in a solvent, which can be e.g. dichloromethane, dichloroethane, chlorobenzene or mixtures thereof.

B) For the preparation of compound of formula (VI) and pharmaceutically acceptable salts thereof

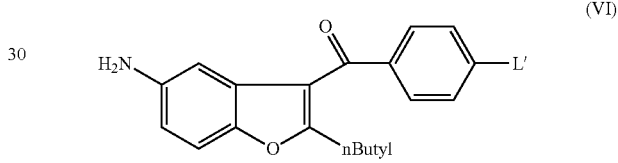

a compound of formula (VII)

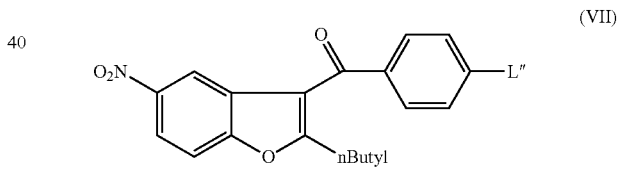

is hydrogenated, where L' and L" is a leaving group, and the obtained product is isolated and, if desired, converted into a pharmaceutically acceptable salt thereof.

The meaning of L' can be selected from the following group: halogen, alkylsulfonyloxy, optionally substituted with one or more halogen (e.g. methanesulfonyloxy, trifluoromethanesulfonyloxy) and arylsulfonyloxy (e.g benzenesulfonyloxy), optionally substituted with halogen, alkyl, alkoxy or amino.

The meaning of L" can be selected from the following group: halogen, alkylsulfonyloxy, optionally substituted with one or more halogen (e.g. methanesulfonyloxy, trifluoromethanesulfonyloxy) and arylsulfonyloxy (e.g benzenesulfonyloxy), optionally substituted with halogen, alkyl, alkoxy or nitro.

The hydrogenation of compound of formula (VII) is carried out in a solvent or mixture of solvents, in the presence of a catalyst, which can be e.g. PtO$_2$ or Pd/C. The solvent can be selected from the group C1-C4 alcohols, ethyl acetate, cyclohexane and tetrahydrofurane and mixtures thereof (e.g. ethanol or methanol).

C) For the preparation of compound of formula (II) and pharmaceutically acceptable salts thereof

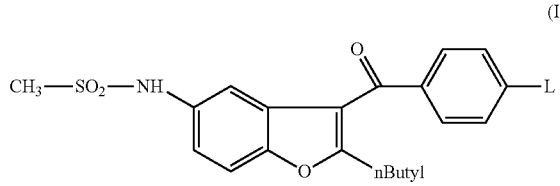

where L is a leaving group, typically halogen, alkylsulfonyloxy, optionally substituted with one or more halogen (e.g. methanesulfonyloxy, trifluoromethanesulfonyloxy) or arylsulfonyloxy (e.g benzenesulfonyloxy), optionally substituted with halogen, alky, alkoxy or alkylsulfonylamino (e.g. methanesulfonylamino), a) when L is halogen, then the compound of formula (IV)

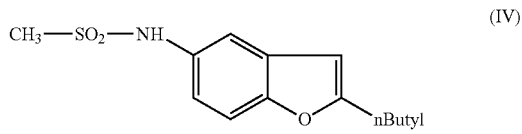

is reacted with a compound of formula (V)

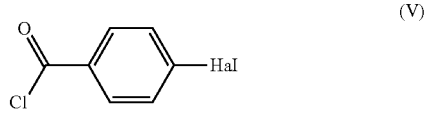

where Hal is halogen, and b) when L is different from halogen, e.g. alkylsulfonyloxy, optionally substituted with one or more halogen (e.g. methanesulfonyloxy, trifluoromethanesulfonyloxy) or arylsulfonyloxy (e.g benzenesulfonyloxy), optionally substituted with halogen, alky, alkoxy or alkylsulfonylamino (e.g. methanesulfonylamino), then a compound of formula (VI)

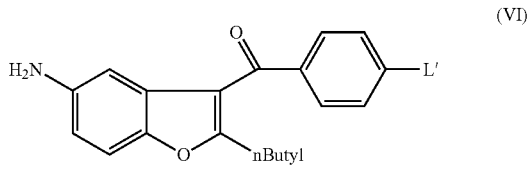

where L' is alkylsulfonyloxy, optionally substituted with one or more halogen (e.g. methanesulfonyloxy, trifluoromethanesulfonyloxy) or arylsulfonyloxy (e.g. benzenesulfonyloxy), optionally substituted with halogen, alky, alkoxy or amino, is mesylated, and the obtained product is isolated and, if desired, converted into a pharmaceutically acceptable salt thereof.

In process variant a) the reaction is carried out under Friedel-Craft reaction conditions (see e.g. in Advanced Organic Chemistry John Wiley and Sons 4. Ed. 1992, 538-42).

The reaction is carried out in halogenated and nitro group containing solvents, e.g. dichloromethane, dichloroethane, chlorobenzene, nitromethane, nitrobenzene. Catalyst also can be applied, typically Lewis acids, e.g. $AlCl_3$, $FeCl_3$, $SnCl_4$, $TiCl_4$.

In process variant b) the mesylation is carried out in a solvent or mixture of inert solvents, typically in the presence of base. The solvent can be selected from the group of halogenated solvents (e.g. dichloromethane, dichloroethane, chlorobenzene), aromatic solvents (e.g. toluene) and ethers (e.g. diisopropyl ether) and mixtures thereof. The base can be selected from group of tercier amines (e.g. pyridine or triethyl amine) and inorganic bases (e.g. carbonates, hydrogen carbonates, alkali hydroxides).

In the process a mesylating reagent should be applied. It can be any reagent which can be used for inserting a $CH_3SO_2$—group into the free amino group of compound of formula (VI). It is practical to use methanesulfonic anhydride or methanesulfonyl halogenide, e.g. methanesulfonyl chloride.

D) Finally, for the preparation of dronedarone of formula (I) and pharmaceutically acceptable salts thereof

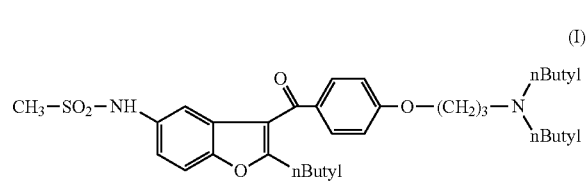

an above compound of formula (II) [where L is leaving group, typically selected from the group of halogen, alkylsulfonyloxy, optionally substituted with one or more halogen (e.g. methanesulfonyloxy, trifluoromethanesulfonyloxy), and arylsulfonyloxy (e.g benzenesulfonyloxy), optionally substituted with halogen, alky, alkoxy or alkylsulfonylamino (e.g. methanesulfonylamino), is reacted with compound of formula (III)

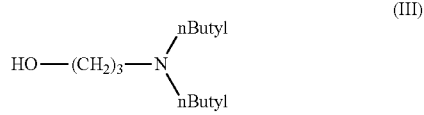

and the obtained product is isolated and, if desired, converted into a pharmaceutically acceptable salt thereof.

Typically the reaction is carried out in solvents in presence of base, optionally in the presence of a catalyst.

The solvent can be e.g. dimethyl formamide, dimethyl sulfoxide, hexamethylphosphoramide, mono- or dialkyl pyridine and similar polar solvents and any mixtures thereof.

In some cases an alkali salt of the compound of formula (III) is used as base.

The catalyst may be for example a copper salt (e.g. copper iodide) or copper oxide catalyst, when L leaving group is halogen. When L is different from halogen, then there is no necessity to use catalyst.

Typically the reaction is carried out in the presence of a base, which can be selected from the group of (alkaline hydroxide, alkaline hydride, alkaline amide, e.g. KOH, NaH, Na-amide.

As used herein, the term alkyl includes straight or branched aliphatic hydrocarbon chains of 1 to 6 carbon atoms, e.g., methyl, ethyl, isopropyl and t-butyl.

As used herein, the term "aryl" includes aromatic monocyclic or multicyclic ring systems comprising 6 to about 14 carbon atoms, preferably 6 to about 10 carbon atoms. Non-limiting examples of suitable aryl groups include phenyl and naphthyl.

As used herein, the term "halogen" includes fluoro, chloro, bromo and iodo atoms.

In the above reactions the temperature is chosen according to the general practice of a person skilled in organic chemistry. Typically the temperature is between 10° C. and the boiling point of the applied solvent (which can be the mixture of the mentioned solvents in a specific embodiment). Applicable temperature values can be found in the examples.

All the above reactions are carried out under atmospheric pressure with the exception of the hydrogenation steps where higher pressure also can be applied, typically up to 20 bar, e.g. 5 to 10 bar.

The applicable acid for the preparation of pharmaceutically acceptable salts can be any inorganic or organic acid which forms an acid addition salt with the compound of general formula (I). Exemplary acids which can form an acid addition salt are as follows: acetic acid, adipic acid, alginic acid, ascorbic acid, aspartic acid, benzoic acid, benzenesulfonic acid, methansulfonic acid, ethansulfonic acid, boric acid, butyric acid, citric acid, ethanesulfonic acid, fumaric acid, hydrogen chloride, hydrogen bromide, hydrogen iodide, 2-hydroxyethanesulfonic acid, maleic acid, oxalic acid, methanesulfonic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compound of general formula (I) (see the "left side" of the molecules) a salt formation can be carried out (on the amide part of it) by a strong base, e.g. an alkaline hydroxide, typically by sodium hydroxide. However, these salts have less practical importance, but they are within the scope of salts. It means that the phrase "salts" embraces both the acid addition salts and the salts formed by bases (basic salts) in case of compounds of general formula (I).

As it was mentioned above the further starting materials are commercially available or can be prepared by applying known synthetic ways, e.g. as it is given in the relating examples.

Other objects of the invention are the novel intermediary compounds applied in the processes, namely the following compounds:

Compounds of formula (II) and pharmaceutically acceptable salts thereof

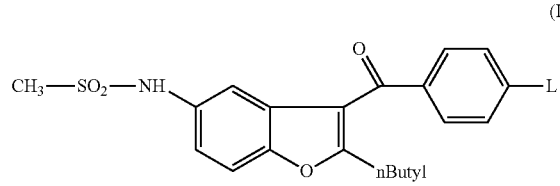

(II)

where L is a leaving group selected from halogen, alkylsulfonyloxy, optionally substituted with one or more halogen, or arylsulfonyloxy, optionally substituted with halogen, alky, alkoxy or alkylsulfonylamino.

In a preferred embodiment the compound of formula (II) is selected from the following group:

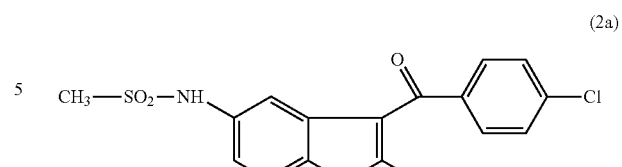
(2a)

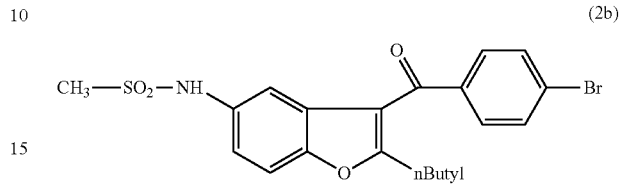
(2b)

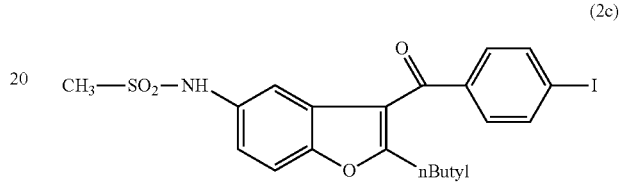
(2c)

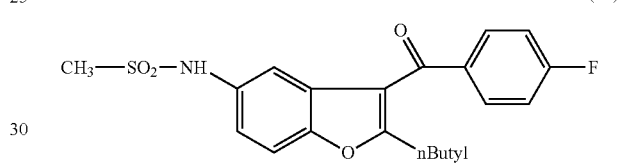
(2d)

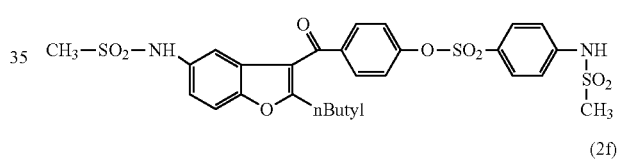
(2e)

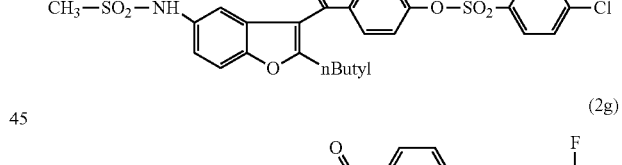
(2f)

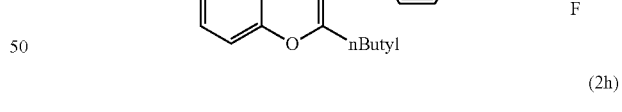
(2g)

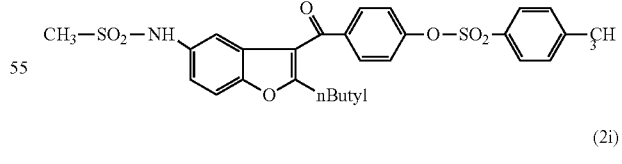
(2h)

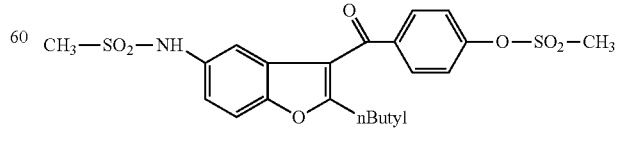
(2i)

Compounds of formula (VI) and pharmaceutically acceptable salts thereof

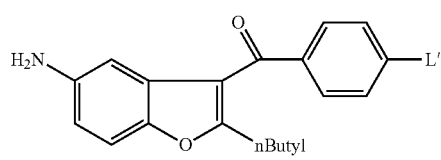
(VI)

where L' alkylsulfonyloxy, optionally substituted with one or more halogen, or arylsulfonyloxy, optionally substituted with halogen, alky, alkoxy or amino.

In a preferred embodiment the compound of formula (VI) is selected from the following group:

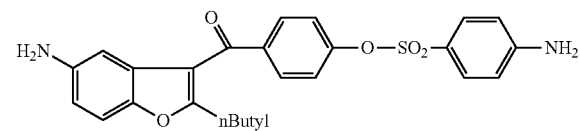
(6e)

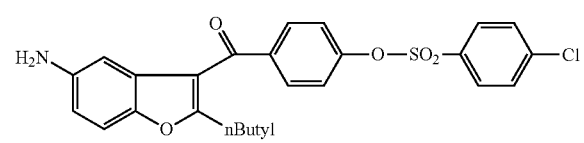
(6f)

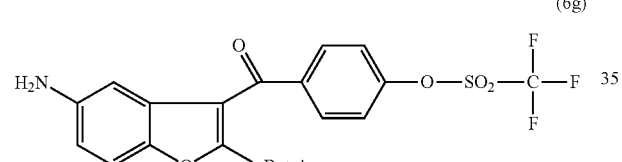
(6g)

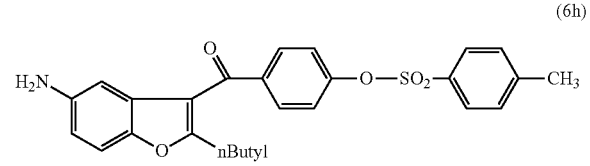
(6h)

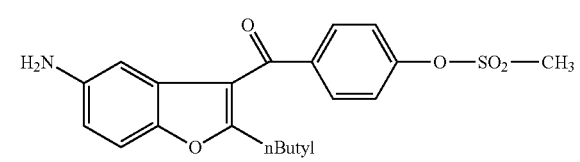
(6i)

Compounds of formula (VII)

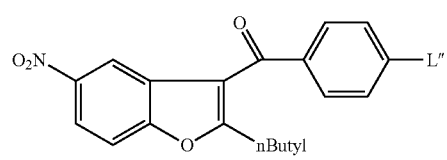
(VII)

where L" is alkylsulfonyloxy, optionally substituted with one or more halogen, or arylsulfonyloxy, optionally substituted with halogen, alky, alkoxy or nitro.

In a preferred embodiment the compound of formula (VII) is selected from the following group:

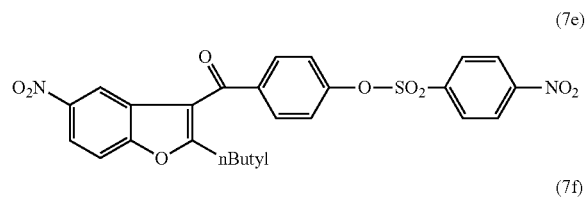
(7e)

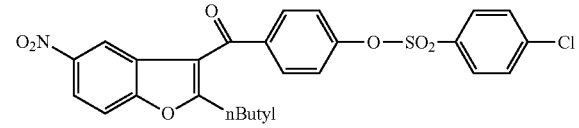
(7f)

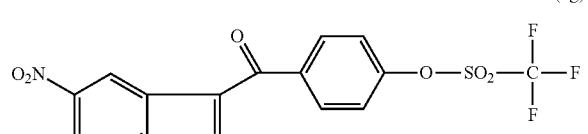
(7g)

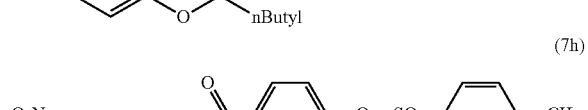
(7h)

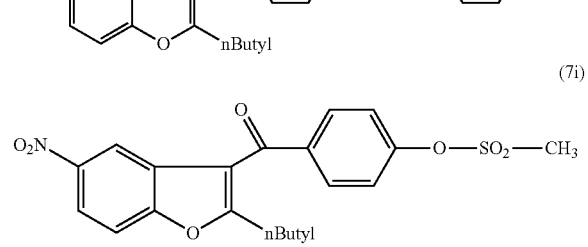
(7i)

Other objects of the invention are the processes for the preparation of the novel intermediary compounds, namely the following ones:

Process for preparation of compounds of formula (II) and pharmaceutically acceptable salts thereof

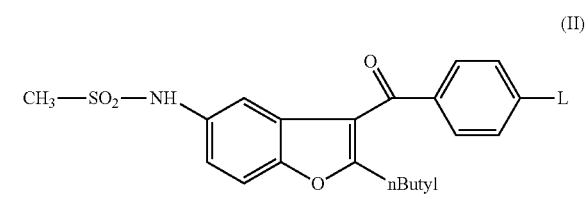
(II)

where L is leaving group, characterized in that
a) when L is halogen, then the compound of formula (IV)

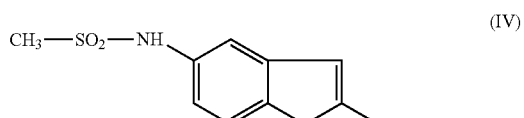
(IV)

is reacted with a compound of formula (V)

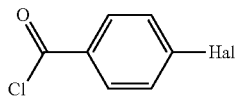

where Hal is halogen, and b) when L is different from halogen, then a compound of formula (VI)

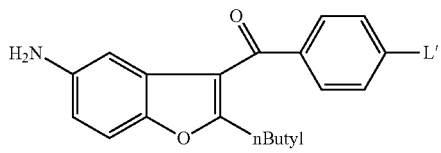

is mesylated, where L' is a leaving group being different from halogen, and the obtained product is isolated and, if desired, converted into a pharmaceutically acceptable salt thereof.

Process for preparation of compounds of formula (VI) and pharmaceutically acceptable salts thereof

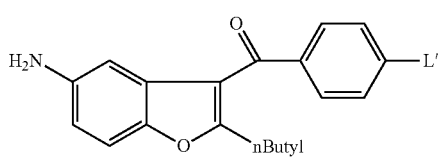

where a compound of formula (VII)

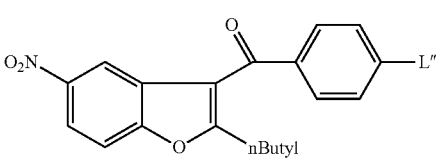

is hydrogenated, where L" is a leaving group, and the obtained product is isolated and, if desired, converted into a pharmaceutically acceptable salt thereof.

Process for preparation of compound of formula (VII)

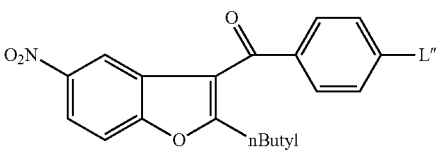

characterized in that the compound of formula (VIII)

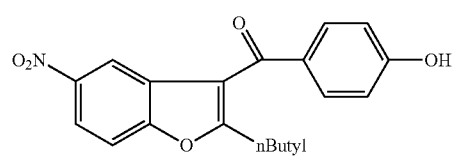

is reacted with activated form of a compound of HO—SO$_7$-L''' (IX),
where L''' is leaving group.

In the processes for the preparation of the intermediary compounds the product is isolated as a base typically (if the compound has an alkylated amino group). If desired, the isolated base can be converted into a salt (acid addition salt) thereof, which is typically a pharmaceutically acceptable salt [the possible acids are mentioned in point D)]. Theoretically the acid addition salt can be prepared directly if the relating acid is in the final reaction mixture from which the solid product is made (however, this way is not applied in case of these compounds where the base type form has practical importance).

Here it is mentioned that some of the above intermediary compounds have a mesylate group (see the "left side" of the molecules) where a salt formation can be carried out (on the amide part of it) by a strong base, e.g. an alkaline hydroxide, typically by sodium hydroxide. However, these salts have less practical importance, but they are within the scope of salts which can be prepared by the claimed process, i.e. the phrase "salts" embraces the salts formed by bases (basic salts) in such cases (where the molecule has a mesylate group).

EXAMPLES

Example 1

N-[2-butyl-3-{4-[(3-dibutylamino)propoxy]benzoyl}-benzofuran-5-yl]-methanesulfonamide (I)

2 g of N-[2-butyl-3-(4-fluorobenzoyl)-1-benzofuran-5-yl])methanesulfonamide (2 d), 1.0 g of powered CuI was added to a solution of 1.1 g of dibutylamino-propanol sodium salt dissolved in 5 ml of dimethylformamide. The mixture was stirred at 90-100° C. for 25 hours. After cooling the solution was filtered. The dimethylformamide was evaporated in reduced pressure. 10 ml of water was added and the mixture was extracted with 10 ml of dichloromethane. The dichloromethane phase was washed at first with 10 ml of sodium carbonate of 5% then with 2×10 ml of water and evaporated. The product was purified by column chromatography on silica gel (eluent: ethyl acetate/hexane 1:3).

Mass of product: 2.86 g (100%).
Purity (HPLC): 99.5%.
$^1$H NMR (DMSO): 0.8-0.9 (m, 9H); 1.2-1.5 (m, 10H); 1.67 (5', 2H); 1.87 (5', 2H); 2.38 (t, J=7.2 Hz, 4H); 2.57 (m, 2H); 2.81 (t, J=7.5 Hz, 2H); 29.91 (s, 3H); 4.15 (t, J=6.2 Hz, 2H); 7.09 (d, J=8.8 Hz, 2H); 7.24 (dd, J=8.9, 2.2 Hz, 1H); 7.34 (d, H=2.1 Hz, 1H); 7.65 (d, J=8.8 Hz, 1H); 7.81 (d, J=8.8 Hz, 2H).

Example 2

N-[2-butyl-3-{4-[(3-dibutylamino)propoxy]benzoyl}-benzofuran-5-yl]-methanesulfonamide (I)

1.7 g of N-[2-butyl-3-(4-chlorobenzoyl)-1-benzofuran-5-yl])methanesulfon-amide (2a), 0.8 g of powered CuI was added to a solution of 1.05 g of dibutylamino-propanol sodium salt dissolved in 8 ml of collidine. The mixture was stirred at 100° C. for 10 hours.

After cooling the solution was filtered and the reaction mixture was evaporated in reduced pressure. 10 ml of water was added and the mixture was extracted with 10 ml of dichloromethane. The dichloromethane phase was washed with 10 ml of sodium carbonate of 5% and with 2×10 ml of water. After drying the dichloromethane was evaporated.

Mass of product: 2.25 g (96.1%). The product was identical with the compound prepared in Example 1.

Example 3

N-[2-butyl-3-{4-[(3-dibutylamino)propoxy]benzoyl}benzofuran-5-yl]-methanesulfonamide (I)

2.1 g of N-[2-butyl-3-(4-iodobenzoyl)-1-benzofuran-5-yl])methanesulfonamide (2c) and 1.14 g of dibutylamino-propanol potassium salt was dissolved in 10 ml of dimethyl-sulfoxide. The mixture was stirred for 30 minutes at 130° C. After cooling to the mixture 15 ml of water was added and extracted with 2×10 ml of dichloromethane. After drying the dichloromethane was evapored and purified using column chromatography on silica gel (eluent: ethyl acetate/hexane 1:3).

Mass of product: 2.1 g (89.7%). The product was identical with the compound prepared in Example 1.

Example 4

N-[2-butyl-3-{4-[(3-dibuylamino)propoxy]benzoyl}-benzofuran-5-yl]-methanesulfonamide (I)

2.7 of N-[2-butyl-3-(4-bromobenzoyl)-1-benzofuran-5-yl])methanesulfonamide (2b) and 1.36 of dibutylamino-propanol potassium salt was dissolved in 25 ml of hexamethylphosphor-amide and the reaction mixture was stirred et 90° C. for 20 hours. The mixture was cooled, 50 ml of water was added and the mixture was extracted with 2×20 ml of dichloromethane. The dichloromethane was evaporated after drying and purified using column chromatography on silica gel (eluent: ethyl acetate/hexane 1:3).

Mass of product: 3.25 g (97.4%)

The product was identical with compound prepared in Example 1.

Example 5

N-[2-butyl-3-{4-[(3-dibutylamino)propoxy]benzoyl}-benzofuran-5-yl]-methanesulfonamide (I)

2.4 g of 4-({2-butyl-5-[methylsulfonyl)amino]-1-benzofuran-3-yl}carbonyl)phenyl-trifluoro-methanesulfonate (2 g) was dissolved in the solution of 0.33 g of potassium hydroxide of 85% in abs. dimethylformamide. After complete dissolution 0.98 g of dibutylamino-propanol was added and the mixture was stirred at 40° C. for 9 hours and cooled down. The solvent was evaporated and the residue was dissolved in 15 ml of dichloromethane. 10 ml of water was added and the mixture was stirred for 5 minutes. The phases were separated. The dichloromethane was washed with 2×10 ml of water and after drying evaporated and purified using column chromatography on silica gel (eluent: ethyl acetate/hexane 1:3).

Mass of product: 2.67 g (93.6%). The product was identical with the compound prepared in Example 1.

Example 6

N-[2-butyl-3-{4[(3-dibutylamino)propoxy]benzoyl}-benzofuran-5-yl]-methanesulfonamide (I)

3 g of 4-({2-butyl-5-[(methylsulfonyl)amino]-1-benzofuran-3-yl}carbonyl)phenyl-4-methyl-benzenesulfonate (2 h) was added to a dispersion prepared from 0.3 g of sodium hydride of 50% dispersed in 10 ml of dimethylformamide. 1.1 g of dibutylamino-propanol was added and the mixture was stirred at 25° C. for 10 hours. The dimethylformamide was evaporated in reduced pressure. 12 ml of water was added and the mixture was extracted with 2×10 ml of dichloromethane. The dichloromethane was washed with 10 ml of sodium carbonate of 5% and with 2×10 ml of water. The solvent was evaporated and purified using column chromatography on silica gel (eluent: ethyl acetate/hexane 1:3).

Mass of product: 2.78 g (92.7%). The product was identical with compound prepared in example 1.

Example 7

N-[2-butyl-3-{4-[(3-dibutylamino)propoxy]benzoyl}-benzofuran-5-yl]-methanesulfonamide (I)

The process according to example 5 was performed with the different that in the reaction 3.2 g of 4-({2-butyl-5-[(methylsulfonyl)amino]-1-benzofuran-3-yl}carbonyl)phenyl-4-[(methyl-sulfonyl)amino]benzenesulfonate (2e) was used as reactant. The product was purified by column chromatography on silica gel (eluent: ethyl acetate/hexane 1:3).

Mass of product: 3.67 g (96.5%). The product was identical with compound prepared in Example 1.

Example 8

N-[2-butyl-3-{4[(3-dibutylamino)propoxy]benzoyl}-benzofuran-5-yl]-methanesulfonamide (I)

The process according to example 6 was performed with the difference that in the reaction 3.1 g of 4-({2-butyl-5-[(methylsulfonyl)amino]-1-benzofuran-3-yl}carbonyl)phenyl-4-chloro-benzenesulfonate (2f) was used as reactant. The product was purified by column chromatography on silica gel (eluent: ethyl acetate/hexane 1:3).

Mass of product: 2.67 g (89.6%). The purified product was identical with compound prepared in Example 1.

Example 9

N-[2-butyl-3-{4-[(3-dibutylamino)propoxy]benzoyl}-benzofuran-5-yl]-methanesulfonamide (I)

The process according example 6 was performed with the difference that in the reaction 2.7 g of 4-({2-butyl-5-[(methylsulfonyl)amino]-1-benzofuran-3-yl}carbonyl)phenyl-methanesulfonate (2i) was used as reactant. The product was purified by column chromatography on silica gel (eluent: ethyl acetate/hexane 1:3).

Mass of product: 2.05 g (89.1%). The product was identical with compound prepared in example 1.

Example 10

N-[2-butyl-3-(4-fluorobenzoyl)-1-benzofuran-5-yl]methanesulfonamide (2d)

3.64 g of 4-fluorobenzoyl-chloride—prepared by reacting 4-fluorbenzoic acid with thionyl chloride—and 5.42 g of 2-butyl-5-methanesulfonylamido-benzofuran (IV) were dissolved in 30 ml of dichloromethane. The solution was cooled to 0 to 5° C. and at this temperature 3.9 g ferrichloride was added in four portions in 20 minutes. The mixture was allowed to warm to room temperature and was stirred at this temperature for four hours. The mixture was warmed to 40° C. and 54 ml of warm water (temperature: apprx. 30-35° C.) was added in 30 minutes. After separation of phases the dichloromethane phase was washed at 40° C. with 16 ml of water, 2×16 ml of sodium hydrocarbonate of 5% and with 2×16 ml of water.

The dichlorometane was evaporated. Mass of product: 6.7 g (89.9%).

This crude product was crystallized in hot isopropanol.

Mass of pure product: 3.19 g (HPLC: 100%). Mp: 151.0-151.9° C.

1H NMR (DMSO): 9.60 (s, 1H); 7.86 (dd, J=8.1, 5.8 Hz, 2H); 7.63 (d, J=8.8 Hz, 1H); 7.39 (t, J=8.7 Hz, 2H); 7.26 (d, J=5.1 Hz, 1H); 7.21 (dd, J=8.8, 1.8 Hz, 1H); 2.88 (s, 3H); 2.79 (t, J=7.5 Hz, 2H); 1.65 (5', J=7.3 Hz, 2H); 1.24 (6', J=7.3 Hz, 2H); 0.80 (t, J=7.3 Hz, 3H).

Example 11

N-[2-butyl-3-(4-iodobenzoyl)-1-benzofuran-5-yl] methanesulfonamide (2c)

6.12 g of 4-iodobenzoyl chloride—prepared by reacting 4-iodobenzoic acid with thionyl chloride—and 5.42 g of 2-butyl-5-methanesulfonamido-benzofuran (IV) were dissolved in 30 ml of dichloromethane. The reaction was performed according to Example 10.

Mass of crude product: 8.65 g (85.8%).

The crude product was crystallized in hot isopropanol.

Mass of pure product: 5.53 g. Purity (HPLC): 100%. Mp: 189.1-190.1° C.

1H NMR (DMSO): 9.61 (s, 1H); 7.95 (d, J=8.6 Hz, 2H); 7.63 (d, J=8.8 Hz, 1H); 7.54 (d, J=8.2, 2H); 7.28 (d, J=1.5 Hz, 1H); 7.22 (dd, J=8.8, 1.8 Hz, 1H); 2.88 (s, 3H); 2.78 (t, J=7.5 Hz, 2H); 1.64 (5', J=7.4 Hz, 2H); 1.23 (6', J=7.4 Hz, 2H); 0.80 (t, J=7.4 Hz, 3H)

Example 12

N-[2-butyl-3-(4-bromobenzoyl)-1-benzofuran-5-yl] methanesulfonamide (2b)

5.08 g of 4-bromobenzoyl chloride—prepared by reacting 4-bromobenzoic acid with thionyl chloride—and 5.42 g of 2-butyl-5-methanesulfonamido-benzofuran (IV) were dissolved in 30 ml of dichloromethane. The reaction was performed according to Example 10.

Mass of crude product: 8.39 g (91.8%).

The crude product was crystallized in hot isopropanol.

Mass of pure product: 5.87 g (HPLC: 100%) Mp: 164.5-165.6° C.

1H NMR (DMSO): 9.61 (s, 1H); 7.78 (d, J=8.4 Hz; 2H); 7.71 (d, J=8.4 Hz, 2H); 7.64 (d, J=8.7 Hz, 1H); 7.27 (d, J=2.4 Hz, 1H); 7.22 (dd, J=2.1, 8.7 Hz, 1H); 2.88 (s, 311); 2.79 (t, J=7.4 Hz, 2H); 1.65 (5', J=7.5 Hz, 2H); 1.24 (6', J=7.4 Hz, 2H); 0.80 (t, J=7.4 Hz, 3H)

Example 13

N-[2-butyl-3-(4-chlorobenzoyl)-1-benzofuran-5-yl] methanesulfonamide (2a)

4.02 g of 4-chlorobenzoyl chloride—prepared by reacting 4-chlorobenzoic acid with thionyl chloride—and 5.42 g of 2-butyl-5-methanesulfonamido-benzofuran (IV) were dissolved in 30 ml of dichloromethane. The reaction was performed according to Example 10.

Mass of crude product: 8.16 g (99.3%).

The crude product was crystallized in hot isopropanol.

Mass of pure product: 4.2 g, (HPLC: 100%) Mp: 151.6-153.2° C.

1H NMR (DMSO): 9.61 (s, 1H); 7.79 (d, J=8.5 Hz, 2H); 7.63 (d, J=8.4 Hz, 3H); 7.27 (d, J=2.1 Hz, 1H); 7.22 (d.d, J=2.2, 8.8 Hz, 1H); 2.88 (s, 3H); 2.79 (t, J=7.5 Hz, 2H); 1.65 (5', J=7.6 Hz, 2H); 1.24 (6', J=7.4 Hz, 2H); 0.81 (t, J=7.4 Hz, 3H)

Example 14

4-[(2-butyl-5-nitro-1-benzofuran-3-yl)carbonyl]phenyltrifluoromethanesulfonate (7 g)

5.0 g of (2-butyl-5-nitro-3-benzofuranyl)(4-hydroxyphenyl)methanon (VIII) was dissolved in 50 ml of dichloromethane and 2.24 g of triethylamine was added under cooling at 20° C. 4.75 g of trifluoromethanesulfonyl anhydride was added in 30 minutes under gentle cooling. The mixture was boiled for 5 hours. After cooling to room temperature the mixture was stirred with 10 ml of sodium carbonate of 10% for 2 hours and the phases were separated. The dichloromethane phase was evaporated.

Mass of residual oil: 7.59 g (109%). The yield is over 100% because of the solvent content of the obtained oil.

Purity (HPLC): 94.9%.

1H NMR (DMSO): 8.30 (d, J=2.3 Hz, 1H); 8.28 (dd, J=8.9, 2.4 Hz, 1H); 8.00 (d, J=8.8 Hz, 1H); 7.95 (d, J=9.0 Hz, 1H); 7.74 (d, J=8.8 Hz, 2H); 2.76 (t, J=7.6 Hz, 2H); 1.66 (5', J=7.7 Hz, 2H); 1.22 (6', J=7.3 Hz, 2H); 0.79 (t, J=7.3 Hz, 3H).

Example 15

4-[(2-butyl-5-amino-1-benzofuran-3-yl)carbonyl] phenyltrifluoromethanesulfonate (6 g)

7.59 g of 4-[(2-butyl-5-nitro-1-benzofuran-3-yl)carbonyl] phenyltrifluoromethanesulfonate (7 g) was dissolved in 80 ml of ethanol. 0.9 g of Pd/C of 10% was added and the mixture was stirred at 75° C. under hydrogen pressure of 10 bars for 6.5 hours. After cooling the catalyst was filtered off and the solvent was evaporated.

Mass of product: 6.8 g (95.8%). Purity (HPLC): 94.1%.

1H NMR (DMSO): 7.91 (d, H=8.7 Hz, 2H); 7.70 (d, J=8.7 Hz, 2H); 7.28 (d, J=8.7 Hz, 1H); 6.60 (m, 2H); 5.0 (w, 2H); 2.62 (t, J=7.6 Hz, 21-1); 1.59 (5', J=7.5 Hz, 2H); 1.2 (m, 214); 0.78 (t, J=7.4 Hz, 3H).

Example 16

4-({2-butyl-5-[(methyl sulfonyl)amino]-1-benzofuran-3-yl}carbonyl)phenyltrifluoromethanesulfonate (2 g)

6.6 g of 4-[(2-butyl-5-amino-1-benzofuran-3-yl)carbonyl] phenyltrifluoromethanesulfonate (6 g) was dissolved in 65 ml of dichloromethane. The mixture was warmed to 30 to 35° C. and 1.3 g of pyridine was added at this temperature in 5 minutes. 1.89 g of methanesulfonyl chloride was added at this temperature in 30 minutes and the mixture was stirred at this temperature for 4 hours. After cooling to 20° C. the mixture was washed with 13 ml of water, 13 ml of HCl of 2.5%, with 13 ml of water, 13 ml of sodium bicarbonate of 5% and with 13 ml of water. The dichlorometane phase was evaporated.

Mass of crude product: 7.2 g (92.8%).

The product was crystallized in hot isopropanol.

Mass of pure product: 5.41 g. Purity (HPLC): 96.5%. Mp: 143.3-144.1° C.

1H NMR (DMSO): 9.63 (s, 1H); 7.95 (d, J=8.8 Hz, 2H); 7.70 (d, J=8.7 Hz, 2H); 7.64 (d, J=8.8 Hz, 1H); 7.35 (d, J=2.1 Hz, 1H); 7.22 (dd, J=8.8, 2.2 Hz, 1H); 2.88 (s, 3H); 2.72 (t, J=7.5 Hz, 2H); 1.63 (5', J=7.7 Hz, 2H); 1.21 (6', J=7.4 Hz, 2H); 0.79 (t, 7.6 Hz, 3H).

Example 17

4-[(2-butyl-5-nitro-1-benzofuran-3-yl)carbonyl]phenyl-4-nitrobenzenesulfonate (7e)

20 g of (2-butyl-5-nitro-3-benzofuranyl)(4-hydroxyphenyl)methanon (VIII) was dissolved in 200 ml of dichloromethane and 8.95 g of triethylamine was added in 5 minutes at 20° C. 19.6 g of 4-nitrobenzenesulfonyl chloride was added at 20° C. in 30 minutes under gentle cooling. The mixture was boiled for 5 hours. After cooling to room temperature the mixture was stirred with 50 ml of sodium carbonate of 10% for 5 hours. Phase separation. The dichloromethane phase was evaporated.

Mass of residual oil: 37.62 g (121.7%). The yield is over 100% because of the solvent content of the obtained oil.

Purity (HPLC): 86.9%.

1H NMR (DMSO): 8.46 (d, J=8.8 Hz, 2H); 8.26 (dd, J=9.0, 2.3 Hz, 1H); 8.21 (m, 3H); 7.93 (d, J=9.0 Hz, 1H); 7.85 (d, J=8.8 Hz, 2H); 7.32 (d, J=8.6 Hz, 2H); 2.74 (t, J=7.6 Hz, 2H); 1.64 (5', J=7.4 Hz, 2H); 1.20 (6', J=7.5 Hz, 2H); 0.78 (t, J=7.5 Hz, 3H)

Example 18

4-[(2-butyl-5-amino-1-benzofuran-3-yl)carbonyl]phenyl-4-aminobenzenesulfonate (6e)

37.44 g of 4-[(2-butyl-5-nitro-1-benzofuran-3-yl)carbonyl]phenyl-4-nitrobenzenesulfonate (7e) was dissolved in 380 ml of ethanol. 4.1 g of Pd/C of 10% was added and the mixture was stirred at 75° C. for 7 hours under hydrogen pressure of 10 bars. After cooling the catalyst was filtered off and the solvent evaporated.

Mass of product: 31.7 g (96%).

Purity (HPLC): 94.4%.

1H NMP (DMSO): 7.73 (d, J=8.6 Hz, 2H); 7.45 (d, J=8.8 Hz, 2H); 7.27 (d, J=9.4 Hz, 1H); 7.17 (d, J=8.61-1z, 2H); 6.63 (d, J=8.8 Hz, 2H); 6.59 (m, 2H); 6.43 (w, 2H); 5.05 (w, 2H); 2.60 (t, J=7.5 Hz, 2H); 1.58 (5', J=7.3 Hz, 2H); 1.18 (m, 2H); 0.78 (t, J=7.3 Hz, 3H).

Example 19

4-({2-butyl-5-[(methylsulfonyl)amino]-1-benzofuran-3-yl}carbonyl)phenyl-4-[(methylsulfonyl)-amino]benzenesulfonate (2e)

4 g of 4[(2-butyl-5-amino-1-benzofuran-3-yl)carbonyl]phenyl-4-aminobenzenesulfonate (6e) was dissolved in 40 ml of dichloromethane. The mixture was warmed to 30 to 35° C. and 1.5 g of pyridine was added at this temperature in 5 minutes. 40 g of methansulfonyl chloride was added at this temperature in 30 minutes and the mixture was stirred for 4.5 hours. After cooling to 20° C. the mixture was washed with 2×80 ml of water, 1×80 ml of sodium bicarbonate of 5% and with 80 ml of water. The phases were separated. The dichloromethane phase was evaporated.

Mass of product: 1.91 g (34%).

Purity (HPLC): 83.3%. M.p.: 91.8-92.7° C.

1H NMR (DMSO): 10.7 (w, 1H); 9.62 (s, 1H); 7.86 (d, J=8.6 Hz, 2H); 7.80 (d, J=8.6 Hz, 2H); 7.63 (d, J=8.7 Hz, 1H); 7.39 (d, J=8.9 Hz, 2H); 7.33 (d, J=1.9 Hz, 1H); 7.23 (d, J=8.6 Hz, 2H); 7.21 (dd, J=8.9, 2.1 Hz, 1H); 3.17 (s, 3H); 2.89 (s, 3H); 2.69 (t, J=7.6 Hz, 2H); 1.61 (5', J=7.3 Hz, 2H); 1.20 (6', J=7.4 Hz, 2H); 0.79 (t, J=7.4 Hz, 3H).

Example 20

4-[(2-butyl-5-nitro-1-benzofuran-3-yl)carbonyl]phenyl-4-chlorobenzenesulfonate (7f)

20 g of (2-butyl-5-nitro-3-benzofuranyl)[4-hydroxyphenyl]methanon (VIII) was dissolved in 200 ml of dichloromethane and 8.95 g of triethylamine was added under cooling at 20° C. 18.66 g of 4-chlorobenzenesulfonyl chloride was added at 20° C. in 30 minutes under gentle cooling. The mixture was boiled for 5 hours. The cooled mixture was washed with 50 ml of sodium carbonate of 10% for 5 hours at 20° C. Phases were separated. The dichloromethane phase was evaporated.

Mass of residual oil: 32.93 g (108.7%). The yield is over 100% because of the solvent content of the obtained oil.

Purity (HPLC): 93.9%.

1H NMR (DMSO): 8.26 (m, 1H); 8.25 (m, 1H); 7.93 (d, J=8.6 Hz, 3H); 7.85 (d, J=8.8 Hz, 2H); 7.76 (d, J=8.8 Hz, 2H); 7.29 (d, J=8.6 Hz, 2H); 2.73 (t, J=7.7 Hz, 2H); 1.64 (5', J=7.4 Hz, 2H); 1.20 (6', J=7.6 Hz, 2H); 0.79 (t, J=7.4 Hz, 3H)

Example 21

4-[(2-butyl-5-amino-1-benzofuran-3-yl)carbonyl]phenyl-4-chlorobenzenesulfonate (6f)

32.8 g of 4-[(2-butyl-5-nitro-1-benzofuran-3-yl)carbonyl]phenyl-4-chlorobenzene-sulfonate (7f) was dissolved in 330 ml of ethanol. 3.6 g of Pd/C of 10% was added and the mixture was stirred at 75° C. under hydrogen pressure of 10 bars for 3 hours. After cooling the catalyst was filtered off and the solvent was evaporated.

Mass of product: 30.6 g (99%).

Purity (HPLC): 97.8%.

1H NMR (DMSO): 7.93 (d, J=8.7 Hz, 2H); 7.77 (d, J=9.0 Hz, 2H); 7.75 (d, J=9.0 Hz, 2H); 7.27 (d, J=8.7 Hz, 1H); 7.24 (d, J=8.7 Hz, 2H); 6.60 (dd, J=2.3, 8.7 Hz, 1H); 6.55 (d, J=2.1 Hz, 1H); 5.05 (w, 2H); 2.61 (t, J=7.5 Hz, 2H); 1.57 (5', J=7.5 Hz, 2H); 1.18 (6', J=7.3 Hz, 2H); 0.78 (t, 7.3 Hz, 3H).

Example 22

4-({2-butyl-5-[(methylsulfonyl)amino]-1-benzofuran-3-yl}carbonyl)phenyl-4-chlorobenzene-sulfonate (20

30.6 g of 4-[(2-butyl-5-amino-1-benzofuran-3-yl)carbonyl]phenyl-4-chlorobenzene-sulfonate (60 was dissolved in 300 ml of dichloromethane. The mixture was warmed to 30 to 35° C. and 5.5 g of pyridine was added at this temperature in 5 minutes. 8 g of methanesulfonyl chloride was added at this temperature in 30 minutes and the mixture was stirred at this temperature for 2 hours. After cooling to 20° C. the mixture was washed with 2×160 ml of water, 1×160 ml of sodium bicarbonate of 5% and with 1×160 ml of water. The dichloromethane phase was almost evaporated (because of foaming the evaporation was not completed). 50 ml of ethanol was added and the mixture was warmed until complete dissolution. After cooling to room temperature it was kept at this temperature overnight. It was filtered, washed with 10 ml of ethanol, dried.

Mass of product: 26.26 g (71.84%).
Purity (HPLC): 100%. M.p.: 121.2-123.3° C.
1H NMR (DMSO): 9.63 (s, 1H); 7.93 (d, J=8.6 Hz, 2H); 7.80 (d, J=8.6 Hz, 2H); 7.77 (d, J=8.6 Hz, 2H); 7.63 (d, J=8.8 Hz, 1H); 7.30 (d, J=1.9 Hz, 1H); 7.25 (d, J=8.6 Hz, 2H); 7.21 (dd, J=8.8, 2.0 Hz, 1H); 2.88 (s, 3H); 2.70 (t, J=7.5 Hz, 2H); 1.62 (5', J=7.5 Hz, 2H); 1.19 (6', J=7.4 Hz, 2H); 0.79 (t, J=7.5 Hz, 3H).

Example 23

4-[(2-butyl-5-nitro-1-benzofuran-3-yl) carbonyl] phenyl-4-methyl-benzenesulfonate (7 h)

20 g of (2-butyl-5-nitro-3-benzofuranyl)[4-hydroxyphenyl]methanon (VIII) was dissolved in 200 ml of dichloromethane. 8.95 g of triethylamine was added in 5 minutes at 20° C. 16.8 g of 4-methylbenzenesulfonyl chloride was added in 30 minutes at 20° C. under cooling. The mixture was boiled for 5 hours. After cooling the mixture was stirred with 70 ml of sodium bicarbonate of 5% for 3.5 hours. Phase separation was performed. The dichloromethane phase was evaporated.

Mass of product: 33.2 g (114.1%). The yield is over 100% because of the solvent content of the obtained oil.
Purity (HPLC): 100%.
1H NMR (DMSO): 8.30 (dd, J=9.1, 2.4 Hz, 1H); 8.27 (d, J=2.9 Hz, 1H); 7.96 (d, J=8.9 Hz, 1H); 7.86 (d, J=8.7 Hz, 2H); 7.82 (d, J=8.3 Hz, 2H); 7.52 (d, J=8.3 Hz, 2H); 7.29 (d, J=8.6 Hz, 2H); 2.77 (t, J=7.5 Hz, 2H); 2.46 (s, 3H); 1.68 (5', J=7.3 Hz, 2H); 1.24 (6', J=7.5 Hz, 2 h); 0.83 (t, J=7.5 Hz, 2H).

Example 24

4-[(2-butyl-5-amino-1-benzofuran-3-yl)carbonyl] phenyl-4-methyl-benzenesulfonate (6 h)

33.1 g of 4-[(2-butyl-5-nitro-1-benzofuran-3-yl) carbonyl]phenyl-4-methylbenzene-sulfonate (7 h) was dissolved in 380 ml of ethanol. 3.9 g of Pd/C of 10% was added and the mixture was stirred at 75° C. for 5 hours under hydrogen pressure of 10 bars. After cooling the catalyst was filtered off and the solvent evaporated.

Mass of product: 28.8 g (100%).
Purity (HPLC): 100%.
1H NMR (DMSO): 7.83 (d, J=8.5 Hz, 2H); 7.77 (d, J=8.7 Hz, 2H); 7.53 (d, J=8.1 Hz, 2H); 7.30 (d, J=8.5 Hz, 1H); 7.24 (d, J=8.8 Hz, 2H); 6.62 (dd, J=2.2, 8.8 Hz, 1H); 6.58 (d, J=2.1 Hz, 1H); 4.99 (wide, 2H); 2.63 (t, J=7.5 Hz, 2H); 2.46 (s, 2H); 1.60 (5', J=7.9 Hz, 2H); 1.21 (6', J=7.5 Hz, 2H); 0.81 (t, J=7.3 Hz, 3H).

Example 25

4-({2-butyl-5-[(methylsulfonyl)amino]-1-benzofuran-3-yl}carbonyl)phenyl-4-methylbenzene-sulfonate (2 h)

30.8 g of 4-[(2-butyl-5-amino-1-benzofuran-3-yl)carbonyl]phenyl-4-methylbenzene-sulfonate (6 h) was dissolved in 300 ml of dichloromethane. The mixture was warmed to 30 to 35° C. and 5.8 g of pyridine was added at this temperature in 5 minutes. 8.4 g of methanesulfonyl chloride was added at this temperature in 30 minutes and the mixture was stirred at this temperature for 2.5 hours. After cooling to 20° C. the mixture was washed with 2×160 ml of water, 1×160 ml of sodium bicarbonate of 5% and 1×160 ml water. The dichloromethane phase was evaporated.

Mass of residual material: 32.8 g (88.5%).
Purity (HPLC): 97.8%.
1H NMR (DMSO): 9.66 (s, 1H); 7.82 (d, J=8.6 Hz, 4H); 7.66 (d, J=8.6 Hz, 1H); 7.53 (d, J=8.0 Hz, 2H); 7.34 (d, J=2.1 Hz, 1H); 7.25 (m, 3H); 3.21 (d, J=5.2 Hz, 1H); 2.91 (s, 3H); 2.73 (t, J=7.5 Hz, 2H); 2.45 (s, 3H); 1.65 (m, J=7.3 Hz, 2H); 1.23 (m, 2H); J=7.4 Hz, 3H).

Example 26

4-[(2-butyl-5-nitro-1-benzofuran-3-yl) carbonyl] phenyl-methanesulfonate (7i)

20 g of (2-butyl-5-nitro-3-benzofuranyl)[4-hydroxyphenyl]methanon (VIII) was dissolved in 200 ml of dichloromethane. 8.95 g of triethylamine was added in 5 minutes at 20° C. 10.1 g of methanesulfonyl chloride was added in 30 minutes at 20° C. under cooling. The mixture was boiled for 12 hours. After cooling the mixture was stirred with 50 ml of sodium bicarbonate of 5% for 2 hours and with 50 ml of water. The phases were separated. The dichlorometane phase was evaporated.

Mass of product: 24.86 g (100%).
Purity (HPLC): 100%.
1H NMR (DMSO): 8.32 (s, 1H); 8.31 (dd, J=9.0, 2.0 Hz, 1H); 7.98 (d, J=8.6 Hz, 2+1H); 7.61 (d, J=8.5, 1.8 Hz, 1H); 3.53 (s, 3H); 2.83 (t, J=7.6 Hz, 2H); 1.71 (5', J=7.6 Hz, 2H); 1.27 (6', J=7.5 Hz, 2H); 0.83 (t, J=7.4 Hz, 3H).

Example 27

4-[(2-butyl-5-amino-1-benzofuran-3-yl)carbonyl] phenyl-methanesulfonate (6i)

24.5 g of 4-[(2-butyl-5-nitro-1-benzofuran-3-yl) carbonyl]phenyl-4-methanesulfonate (7i) was dissolved in 125 ml of ethanol. 8.6 g of Pd/C of 10% was added and the mixture was stirred at 55° C. for 31 hours under hydrogen pressure of 10 bars. After cooling the catalyst was filtered off and the solvent evaporated.

Mass of product: 22.1 g (99%).
Purity (HPLC): 96.0%.
1H NMR (DMSO): 7.92 (d, J=8.6 Hz, 2H); 7.62 (wide, 1H); 7.58 (d, J=8.6 Hz, 2H); 7.08 (wide, 1H); 6.99 (wide, 1H); 3.52 (s, 3H); 2.75 (t, J=7.8 Hz, 2H); 1.76 (5', J=7.3 Hz, 2H); 1.25 (6', J=7.5 Hz, 2H); 0.83 (t, J=7.5 Hz, 3H).

Example 28

4-({2-butyl-5-[(methylsulfonyl)amino]-1-benzofuran-3-yl}carbonyl)phenyl-methanesulfonate (2i)

12.4 g of 4-[(2-butyl-5-amino-1-benzofuran-3-yl)carbonyl]phenyl-methanesulfonate (6i) was dissolved in 124 ml of dichloromethane. The mixture was warmed to 30 to 35° C. and 2.8 g pyridine was added at this temperature in 5 minutes. 4.0 g of methanesulfonyl chloride was added at this temperature in 30 minutes and the mixture was stirred at 30 to 35° C. for 1 hour. After cooling to 20° C. the mixture was washed with 60 ml of hydrochloric acid solution of 5%, with 60 ml of water, 60 ml of sodium bicarbonate of 5% and with 60 ml of water. The phases were evaporated.

Mass of product: 11.52 g (77.1%).

The product was crystallized in 80 ml of hot methanol.

Mass of pure product: 9.18 g.

Purity (HPLC): 100%. M.p.: 168.9-170.7° C.

1H NMR (DMSO): 9.62 (s, 1H); 7.89 (d, J=8.7 Hz, 2H); 7.64 (d, J=8.8, 1H); 7.53 (d, J=8.6, 2H); 7.29 (d, J=2.1, 1H); 7.21 (dd, J=8.8, 2.21H); 3.47 (2,3H); 2.88 (s, 3H); 2.79 (t, J=7.5, Hz, 2H); 1.65 (5', J=7.5 Hz, 2H); 1.24 (6', J=7.4 Hz, 2H); 0.81 (t, J=7.3 Hz, 3H).

The invention claimed is:

1. A process for the preparation of dronedarone (I), or a pharmaceutically acceptable salt thereof,

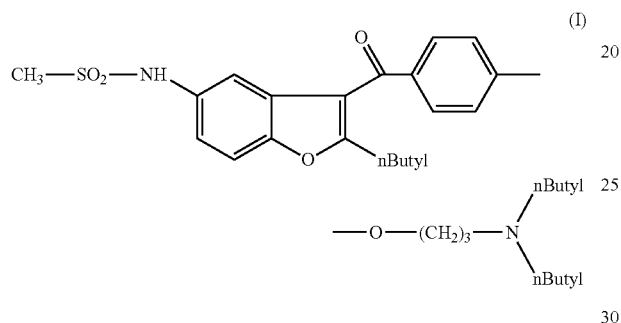

comprising the steps of:
a) reacting a compound of formula (II)

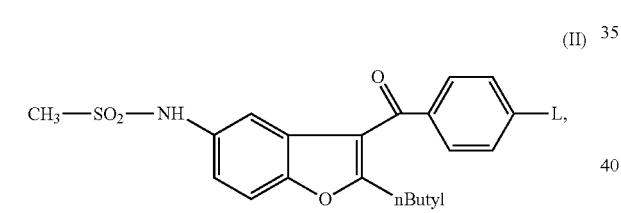

where L is a leaving group, with a compound of formula (III)

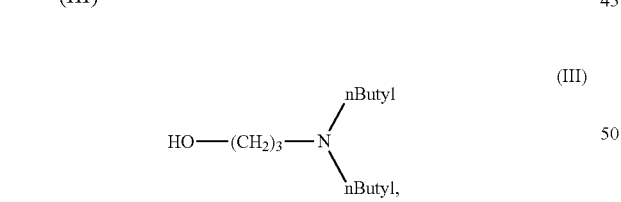

or an alkali salt thereof;
b) isolating dronedarone (I); and
c) optionally converting dronedarone (I) into a pharmaceutically acceptable salt thereof.

2. The process of claim 1, where L is halogen, alkylsulfonyloxy, optionally substituted with one or more halogen, or arylsulfonyloxy, optionally substituted with halogen, alkyl, alkoxy or alkylsulfonylamino.

3. The process of claim 1, where the reaction of step a) is carried out in one or more solvents in the presence of base, and optionally in the presence of a catalyst.

4. The process of claim 1, further comprising a process for the preparation of the compound of formula (II)

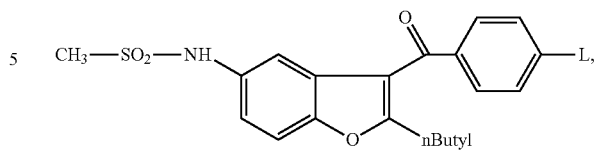

wherein:
when L is different from halo, a compound of formula (VIII)

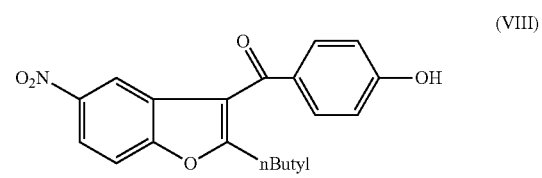

is reacted with an activated form of a compound HO—SO$_2$-L''' (IX), where L''' is alkyl or halogenated alkyl group or aryl group optionally substituted by halogen, alkyl, alkoxy or nitro group, to obtain a compound of formula (VII)

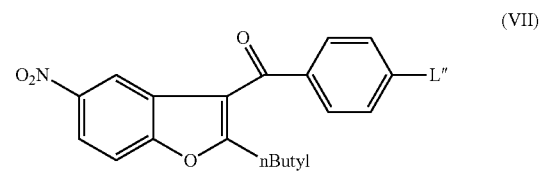

where L" is alkylsulfonyloxy, optionally substituted with one or more halogen, or arylsulfonyloxy, optionally substituted with halogen, alkyl, alkoxy or nitro;
the obtained compound of formula (VII) is hydrogenated to obtain a compound of formula (VI)

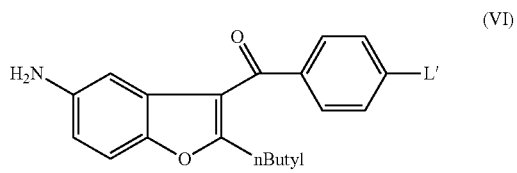

where L' is alkylsulfonyloxy, optionally substituted with one or more halogen, or arylsulfonyloxy, optionally substituted with halogen, alkyl, alkoxy or amino; and
the obtained compound of formula (VI) is mesylated to obtain the compound of formula (II).

5. The process of claim 1, further comprising a process for the preparation of the compound of formula (II)

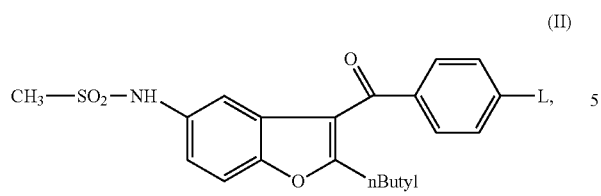
wherein:
when L is halo, a compound of formula (IV)
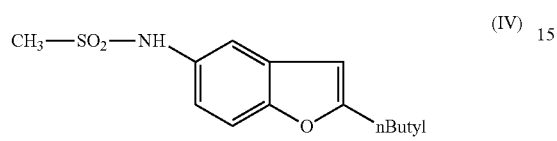
is reacted with a compound of formula (V)
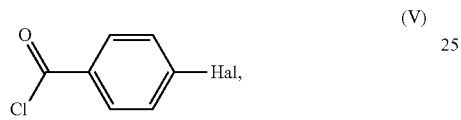
where Hal is halogen, to obtain the compound of formula (II).
* * * * *